United States Patent
Wright

Patent Number: 5,499,628
Date of Patent: Mar. 19, 1996

[54] MEDICAL ELECTRODE

[75] Inventor: Richard A. Wright, Westminster, Mass.

[73] Assignee: Micron Medical Products, Inc., Fitchburg, Mass.

[21] Appl. No.: 113,420

[22] Filed: Aug. 27, 1993

[51] Int. Cl.$^6$ ............................................. A61B 5/0416
[52] U.S. Cl. .................... 128/641; 607/149; 607/153
[58] Field of Search ........................... 128/641; 607/149, 607/152, 153

[56] References Cited

U.S. PATENT DOCUMENTS

| | | | |
|---|---|---|---|
| 3,964,469 | 6/1976 | Manley | 128/2.1 E |
| 3,976,055 | 8/1976 | Monter et al. | 128/2.06 E |
| 4,016,869 | 4/1977 | Reichenberger | 128/2.1 E |
| 4,090,760 | 5/1978 | Furey | 339/61 R |
| 4,094,571 | 6/1978 | Benjamin | 339/91 R |
| 4,126,126 | 11/1978 | Bare et al. | 128/2.06 E |
| 4,165,141 | 8/1979 | Williams et al. | 339/75 R |
| 4,166,456 | 9/1979 | Wilson | 128/640 |
| 4,197,851 | 4/1980 | Fellus | 128/422 |
| 4,282,878 | 8/1981 | Novello | 128/641 |
| 4,304,453 | 12/1981 | Grunwald | 339/75 R |
| 4,317,278 | 3/1982 | Carmon et al. | 29/878 |
| 4,365,634 | 12/1982 | Bare et al. | 128/640 |
| 4,367,755 | 1/1983 | Bailey | 128/798 |
| 4,370,984 | 2/1983 | Cartmell | 128/640 |
| 4,401,356 | 8/1983 | Bare | 339/258 R |
| 4,458,696 | 7/1984 | Larimore | 128/798 |
| 4,539,996 | 9/1985 | Engel | 128/640 |
| 4,543,958 | 10/1985 | Cartmell | 128/640 |
| 4,556,051 | 12/1985 | Maurer | 128/1.5 |
| 4,570,637 | 2/1986 | Gomes et al. | 128/641 |
| 4,681,497 | 7/1987 | Berecz | 411/377 |
| 4,685,467 | 8/1987 | Cartmell et al. | 128/641 |
| 4,742,828 | 5/1988 | Sundstrom | 128/641 |
| 4,915,656 | 4/1990 | Alferness | 439/729 |
| 5,199,432 | 4/1993 | Quedens et al. | 128/642 |
| 5,265,579 | 11/1993 | Ferrari | 128/640 |
| 5,355,883 | 10/1994 | Ascher | 128/641 |

FOREIGN PATENT DOCUMENTS

| | | |
|---|---|---|
| 1144606 | 4/1983 | Canada . |
| 0210020 | 1/1987 | European Pat. Off. . |
| 0510786 | 10/1992 | European Pat. Off. . |
| 9316259 | 2/1994 | Germany . |
| 2203344 | 10/1988 | United Kingdom . |
| 9111834 | 8/1991 | WIPO ................................ 128/641 |

*Primary Examiner*—Lee S. Cohen
*Attorney, Agent, or Firm*—Bromberg & Sunstein

[57] ABSTRACT

A medical electrode having a resilient terminal press fit onto an eyelet. The eyelet is plastic and has a conductive coating thereon. The terminal is made of a resilient nonmetallic composition, such as a polypropylene blend loaded with carbon fiber. An electrolyte composition is spread upon the bottom of the eyelet for making electrical contact with the skin of a patient. The eyelet, the terminal and the electrolyte composition are preferably all at least translucent to x-rays.

62 Claims, 1 Drawing Sheet

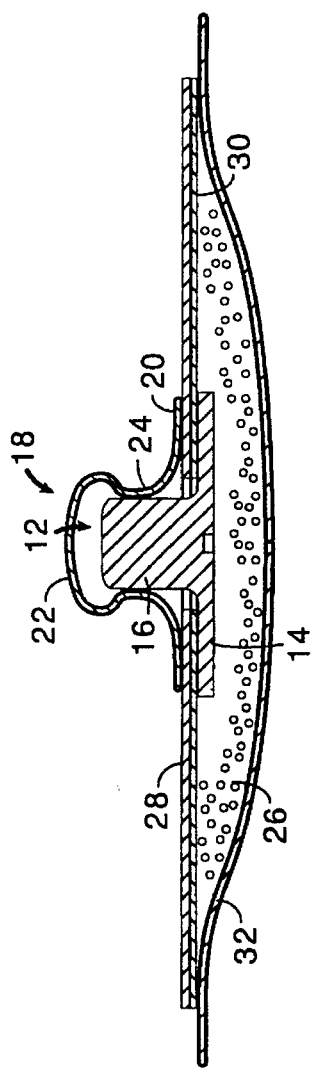
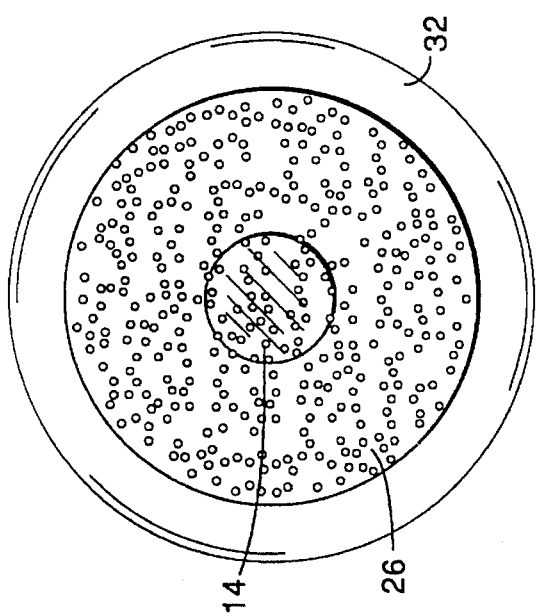
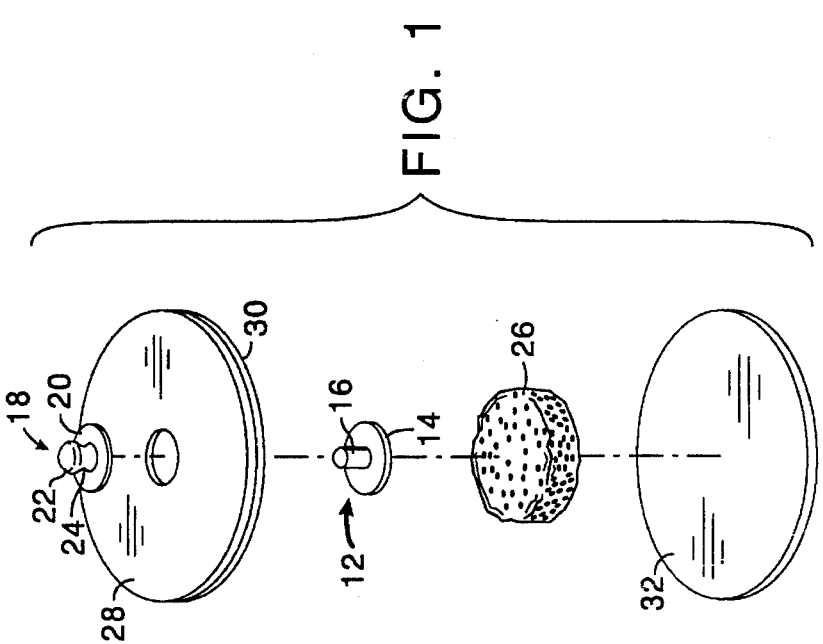
FIG. 1
FIG. 2
FIG. 3

MEDICAL ELECTRODE

BACKGROUND OF THE INVENTION

The present invention is directed to a medical electrode for temporary adhesive placement on a patient. More particularly, this invention relates to a two piece conductor adapted for interconnection between an electrolyte and suitable signal processing or monitoring equipment.

U.S. Pat. No. 3,964,469 describes a disposable electrode having a two piece conductor in contact with a pad. The part of the conductor in contact with the gel pad is a silver plated plastic snap fastener eyelet. The second part of the conductor is a conventional metal snap fastener stud.

U.S. Pat. No. 3,976,055 discloses an electrode with a conductor that can be molded in one piece. The conductor formed in one piece is made of a plastic rendered conductive by including carbon and a modest percentage of metal particles. The patent further discloses an alternate embodiment in which a second part of the conductor includes a conventional metal snap fastener that is press fit onto the first conductor. The two piece conductor disclosed in both patents recited herein will interfere with an x-ray.

SUMMARY OF THE INVENTION

In accordance with the present invention, a new electrode terminal replaces the metal snap of the prior art. The electrode terminal of the invention is a conductor made from a conductive resilient nonmetallic composition. The composition may be a resilient plastic composition loaded with carbon fiber. The other conductive part into which the terminal is press fit is a metallic coated plastic eyelet. The resilient terminal is advantageously less likely to shear off portions of the metallic coating on the eyelet when press fit thereon as compared with a rigid terminal such as one made of metal or ABS.

The metallic coating on the eyelet is made from either silver or silver salt. The thickness of the coating is sufficient to provide the necessary conductivity, but is thin enough to substantially avoid interfering with x-rays. The entire electrode of the present invention is translucent to x-rays. The design of a two-piece x-ray translucent electrode is able to take advantage of the abundant manufacturing capacity of existing two-piece electrode assembly machines.

Other objects and advantages of the invention will become apparent during the following description of the presently preferred embodiment of the invention taken in conjunction with the drawings.

BRIEF DESCRIPTION OF THE DRAWINGS

FIG. 1 an exploded view of a medical electrode of the present invention.

FIG. 2 is side cross section view of the medical electrode of FIG. 1.

FIG. 3 a bottom plan view of the medical electrode of FIG. 1.

DETAILED DESCRIPTION OF THE PREFERRED EMBODIMENT

Referring now to the drawings, the present invention shall be described in the context of a conventional electrode arrangement as shown in FIGS. 1, 2 and 3. The electrode arrangement discussed herein has been selected for illustration purposes only and is not meant to limit the scope of the invention to use therein. Rather, the terminal and two part conductor of the invention may be used in any of a wide variety of electrode arrangements. Machinery for producing medical electrodes with two part conductors is commonly available in the industry.

A first conductor is formed by an eyelet 12. The eyelet 12 is formed of a disc 14 and a post 16 sticking up from the disc 14. The bottom surface of the disc 14 provides a surface area for mounting proximate to the skin of a patient. The eyelet 12 is generally made from plastic. The plastic may be mixed with a conductive material. The eyelet is formed in a mold. In the presently preferred embodiment, the eyelet is made from acrylic butylstyrene (ABS) loaded with glass of about 20% by weight. A conductive layer is coated about the plastic eyelet 12. Preferably, the conductive coating is made from silver or a silver salt such as silver chloride. The conductivity of the eyelet must satisfy AAMI standards in order to prevent loss of ECG readings from the patient during and after defibrillation. In accordance with the present invention, the thickness of the conductive coating is preferably thin enough to be at least x-ray translucent (if not transparent) and yet thick enough to provide sufficient conductivity to meet the safety requirement for defibrillation. The thickness of the metallic coating should be within the range of from 0.02 to 0.10 mils depending largely upon the conductivity of the eyelet material. In accordance with the presently preferred embodiment, the conductive coating is 0.065 mils in thickness. The presently preferred method for coating the plastic eyelet with the silver or silver chloride is through the use of electroless plating. Conventional electroplating may be used instead of or in addition to electroless plating to get the desired coating thickness. Another alternative coating method is to spray a silver-silver chloride ink on the plastic eyelet.

A second conductor is used as the terminal 18 of the electrode. The terminal 18 is shaped as a hollow stud that can be press fit onto the post 16 of the plastic eyelet 12. The hollow stud of terminal 18 sits atop an annular disc 20 having a hole therein. The hollow stud is preferably formed integral with the annular disc in a mold. The hollow stud includes a top crown portion 22 and a bottom waist portion 24. The bottom waist portion 24 extends up from the annular disc 20 and encircles the hole in the disc. The top crown portion 22 is preferably wider in circumference than the base waist portion 24 of the stud. The top crown 22 portion may thus be grabbed onto by an electrical apparatus for making a sufficiently secure electrical connection. The hollow cavity within the stud has a sufficiently small inner diameter to snugly fit about the post 16 of the plastic eyelet 12.

The terminal 18 of the present invention is made from a conductive resilient composition. The terminal 18 is resilient so that when it is press fit, i.e., snapped onto, the plastic eyelet, the metallic coating on the plastic eyelet remains substantially intact. Another advantage of using a resilient material is so that when it is press fit over the post 16, the terminal does not crack.

In addition, the terminal 18 of the invention is nonmetallic so that it is at least translucent to x-rays. The presently preferred composition for the terminal 18 is a plastic composition loaded with a conductive material, such as carbon fiber. In particular, the presently preferred plastic is a polypropylene and carbon 50-50 blend loaded with carbon fibers to about 20% by weight. It has been found that the polypropylene blend loaded with carbon fibers provides sufficient conductivity and is sufficiently resilient to form a tight fit over the post 16 without cracking when it is press fit thereover.

In order to provide a conductive path to the skin of a patient, an electrolyte composition 26 is applied about the bottom surface of the eyelet 12. The electrolyte composition 26 is generally a gel or jelly, either by itself or soaked throughout a pad of cellular material. Suitable conductive gels for this purpose are well known in the art. Commonly used gel materials for providing the conductive path from the bottom surface of the eyelet to the skin include hydrogel, adhesive gel and liquid gel. Any of these commonly used gels or equivalents may be combined with the two part conductor of the present invention to form an electrode.

The terminal 18 should fit tightly over the post 16 on the eyelet. Metallic terminals in conventional two-part electrodes have been known to fail to meet the defibrillation recovery standards when gel seeps between the terminal and the eyelet. This is due to a battery effect. The resilient nonmetallic terminal is less apt to fail due TO such gel seepage.

In order to keep the electrolyte 26 beneath the electrode, a nonporous separator sheet 28 is mounted between the disc of the terminal 18 and the disc of the eyelet. The nonporous sheet 28 may also serve to provide a location on which a manufacturer can indicate its name for the product.

The composition of the electrode of the invention can also be defined electrically. The metallic coating on the eyelet 12 and the conductive material in the terminal 18 provides sufficient conductivity so that the completed electrode has an AC impedance at 10 Hz of less than 200 ohms before and after performing a defribillation. The conductivity can be adjusted by changing the thickness of the metallic coating on the eyelet 12 and/or the quantity of conductive material in the terminal 18.

In order to keep the electrode on the skin of a patient, an adhesive is generally included on the electrode. The electrolyte 26 may itself be an adhesive gel. While this may be sufficient, typically, an adhesive layer 30 is a part of the electrode. A common arrangement is to provide an adhesive layer 30 on the underside of the nonporous sheet 28. Before the electrode is put into use, a removable backing sheet 32 covers the adhesive layer 30. In the simple electrode arrangement shown in the drawings, the backing sheet 32 is made of a nonporous transparent plastic so as to prevent the electrolyte composition from leaking through.

Alternative electrode arrangements may include a plastic foam ring. In this case, the adhesive layer may be provided on the bottom side of the foam ring. The top side of the foam ring is firmly adhered to the nonporous separator sheet. The foam makes a ring around the electrolyte composition.

To use the electrode of the present invention, the removable backing sheet 32 is peeled off the bottom of the electrode revealing the electrolyte composition. The electrolyte composition 20 remains stuck to the bottom surface of the disc on the eyelet 12. The electrode can then be pressed against the skin. The adhesive in the electrolyte composition or the adhesive layer 30 serves to hold the electrode to the skin. The electrolyte 20 provides electrical conductivity between the skin and the two part conductor. All pieces of the electrode of the present invention are advantageously at least translucent to x-rays so that x-ray photos of the patient can be made without the removal of the electrodes. The electrode of the present invention is advantageously made with a two part conductor so that the assembly machines commonly available in the industry may be used in the assembly of the x-ray translucent electrode.

Of course, it should be understood that various changes and modifications to the preferred embodiment described above will be apparent to those skilled in the art. For example, there are many ways to arrange an electrode with a two part conductor mounted therein. The electrode may include a foam ring, a plastic reservoir cover for the electrolyte and paper backing sheets. These and other changes can be made without departing from the spirit and scope of the invention and without diminishing its attendant advantages. It is therefore intended that such changes and modifications be covered by the following claims.

What is claimed is:

1. An electrode, mountable on skin, comprising:
    a first solid conductor for being mounted proximate to the skin, said first solid conductor having a conductive metallic surface;
    a second solid conductor, in electrical communication with said first solid conductor, and permanently mounted thereto, for providing a terminal, said second solid conductor being made of a conductive resilient composition; and
    means for adhering said first solid conductor proximate to the skin.

2. The electrode of claim 1 wherein the conductive resilient composition of the second solid conductor is a resilient plastic composition loaded with a conductive material.

3. The electrode of claim 2 wherein the conductive material is carbon fiber.

4. The electrode of claim 2 wherein the plastic composition comprises polypropylene.

5. The electrode of claim 2 wherein the second conductor includes sufficient conductive material such that said electrode has an AC impedance at 10 Hz of less than 200 ohms before and after a defibrillation.

6. The electrode of claim 1 wherein said first solid conductor comprises a metallic coated plastic eyelet.

7. The electrode of claim 6 wherein the metallic coating on the plastic eyelet comprises at least one component selected from the group consisting of silver and a silver salt.

8. The electrode of claim 6 wherein the metallic coating has a thickness between 0.02 and 0.1 mils.

9. The electrode of claim 6 wherein said second solid conductor comprises a stud press fit onto said eyelet.

10. The electrode of claim 1 wherein said means for adhering comprises an electrolyte composition spread over a bottom surface of said first solid conductor.

11. The electrode of claim 1 further comprising a nonporous layer mounted between said first solid conductor and said second solid conductor.

12. The electrode of claim 11 wherein said means for adhering comprises an adhesive layer on said nonporous layer.

13. The electrode of claim 12 further comprising a removable backing sheet covering the adhesive layer.

14. The electrode of claim 1 wherein said first and second solid conductors are at least translucent to x-rays.

15. An electrode, mountable on skin, comprising:
    a first solid conductor, at least translucent to x-rays, for being mounted proximate the skin, said first solid conductor having a conductive metallic surface;
    a terminal, in electrical connection with said first solid conductor and permanently mounted thereto, said terminal being made of a conductive resilient composition that is at least translucent to x-rays such that said electrode as a whole including said first solid conductor and said terminal is at least translucent to x-rays; and
    adhering means for adhering said first solid conductor proximate to the skin.

16. The electrode of claim 15 wherein the conductive resilient composition is a plastic composition loaded with carbon fiber.

17. The electrode of claim 16 wherein the plastic composition is loaded with at least about 20% by weight of carbon fiber.

18. The electrode of claim 16 wherein the plastic composition comprises polypropylene.

19. The electrode of claim 15 wherein the conductive resilient composition includes sufficient conductive material such that said electrode has an AC impedance at 10 Hz of less than 200 ohms before and after a defibrillation.

20. The electrode of claim 15 wherein said first solid conductor comprises a metallic coated plastic eyelet.

21. The electrode of clam 20 wherein the metallic coating on the plastic eyelet comprises at least one component selected from the group consisting of silver and a silver salt.

22. The electrode of claim 21 wherein the metallic coating has a thickness between 0.02 and 0.1 mils.

23. The electrode of clam 20 wherein said terminal comprises a stud press fit onto said eyelet.

24. The electrode of clam 20 wherein said adhering means comprises an electrolyte composition spread over a bottom surface of said first solid conductor.

25. The electrode of claim 15 further comprising a nonporous layer mounted between said first solid conductor and said terminal.

26. The electrode of claim 25 wherein said adhering means comprises an adhesive layer spread on said nonporous layer.

27. The electrode of claim 26 further comprising an electrolyte composition spread over a bottom surface of said first solid conductor.

28. The electrode of claim 26 further comprising a removable backing sheet covering the adhesive layer.

29. An electrode mountable on skin comprising:
a plastic eyelet including a disc with a bottom surface and a post sticking up from the disc;
a conductive layer coating said plastic eyelet;
a terminal shaped as a hollow stud press fit onto the post of said plastic eyelet, made of a conductive resilient non-metallic composition; and
an electrolyte composition spread upon the bottom surface of said plastic eyelet.

30. The electrode of claim 25 wherein the conductive resilient non-metallic composition is a plastic composition loaded with carbon fiber.

31. The electrode of claim 30 wherein the plastic composition is loaded with at least about 20% by weight of carbon fiber.

32. The electrode of claim 30 wherein the plastic composition comprises polypropylene.

33. The electrode of claim 30 wherein said conductive layer has a thickness of between 0.02 and 0.1 mils.

34. The electrode of claim 33 wherein the conductive resilient non-metallic composition includes sufficient conductive material such that said electrode has an AC impedance at 10 Hz of less than 200 ohms before and after a defibrillation.

35. The electrode of claim 29 wherein said conductive layer on said plastic eyelet comprises at least one component selected from the group consisting of silver and a silver salt.

36. The electrode of claim 29 further comprising a nonporous sheet mounted between the disc of said plastic eyelet and said terminal.

37. The electrode of claim 29 wherein said conductive layer, said electrolyte composition and said terminal are at least translucent to x-rays.

38. The electrode of claim 29 wherein said electrode as a whole including said plastic eyelet, said conductive layer coating, said terminal and said electrolyte composition is at least translucent to x-rays.

39. An electrode, mountable on skin, comprising:
a metallic coated plastic eyelet for being mounted proximate to the skin;
a stud, press fit onto said eyelet in electrical communication with said eyelet, for providing a terminal, said stud being made of a conductive resilient composition; and
means for adhering said eyelet proximate to the skin.

40. The electrode of claim 39 wherein said electrode as a whole including said metallic coated plastic eyelet and said stud is at least translucent to x-rays.

41. An electrode, mountable on skin, comprising:
a plastic eyelet including a disc with a bottom surface and a post sticking up from the disc;
a conductive layer coating said plastic eyelet;
a stud, press fit onto said eyelet for providing a terminal, said stud being in electrical communication with said conductive layer, said stud being made of a material that is conductive, resilient and at least translucent to x-rays such that said electrode as a whole including said coated plastic eyelet and said stud is at least translucent to x-rays; and
adhering means for adhering said eyelet proximate to the skin.

42. An electrode, mountable on skin, comprising:
a first solid conductor for being mounted proximate to the skin;
a second solid conductor, in electrical communication with said first solid conductor and permanently mounted thereto, for providing a terminal, said second solid conductor being made of a conductive resilient composition;
a nonporous layer mounted between said first conductor and said second conductor; and
means for adhering said first solid conductor proximate to the skin.

43. The electrode of claim 42 wherein said means for adhering comprises an adhesive layer on said nonporous layer.

44. The electrode of claim 43 further comprising a removable backing sheet covering the adhesive layer.

45. The electrode of claim 42 wherein the conductive resilient composition of the second conductor is a resilient plastic composition loaded with a conductive material.

46. The electrode of claim 45 wherein the conductive material is carbon fiber.

47. The electrode of claim 45 wherein the plastic composition comprises polypropylene.

48. The electrode of claim 45 wherein said second solid conductor includes sufficient conductive material such that said electrode has an AC impedance at 10 Hz of less than 200 ohms before and after a defibrillation.

49. The electrode of claim 42 wherein said first solid conductor comprises a metallic coated plastic eyelet.

50. The electrode of claim 49 wherein the metallic coating on the plastic eyelet comprises at least one component selected from the group consisting of silver and a silver salt.

51. The electrode of claim 49 wherein the metallic coating has a thickness between 0.02 and 0.1 mils.

52. The electrode of claim 49 wherein said second solid conductor comprises a stud press fit onto said eyelet.

53. The electrode of claim 42 wherein said means for adhering comprises an electrolyte composition spread over a bottom surface of said first solid conductor.

54. The electrode of claim 42 wherein said electrode as a whole including said first solid conductor and said second solid conductor is at least translucent to x-rays.

55. An electrode, mountable on skin, comprising:

a first conductor including a solid post extending therefrom, said first conductor for being mounted proximate to the skin;

a second conductor permanently press fit onto the post of said first conductor so that said first conductor and second conductor are in electrical communication, said second conductor providing a terminal and being made of a conductive resilient composition; and means for adhering said first conductor proximate to the skin.

56. The electrode of claim 55 wherein said electrode as a whole including said first conductor and said second conductor is at least translucent to x-rays.

57. The electrode of claim 55 wherein the conductive resilient composition of the second conductor is a resilient plastic composition loaded with a conductive material.

58. The electrode of claim 57 wherein the conductive material is carbon fiber.

59. The electrode of claim 57 wherein the plastic composition comprises polypropylene.

60. The electrode of claim 57 wherein the second conductor includes sufficient conductive material such that said electrode has an AC impedance at 10 Hz of less than 200 ohms before and after a defibrillation.

61. The electrode of claim 55 wherein said means for adhering comprises an electrolyte composition spread over a bottom surface of said first conductor.

62. The electrode of claim 55 further comprising a nonporous layer mounted between said first conductor and said second conductor.

* * * * *